US00PP16869P2

(12) United States Plant Patent
Zerr

(10) Patent No.: US PP16,869 P2
(45) Date of Patent: Jul. 25, 2006

(54) POINSETTIA PLANT NAMED 'FISNOVIRED'

(50) Latin Name: *Euphorbia pulcherrima*
Varietal Denomination: Fisnovired

(75) Inventor: Katharina Zerr, Hohr-Grenzhausen (DE)

(73) Assignee: Florfis AG, Binningen (CH)

( * ) Notice: Subject to any disclaimer, the term of this patent is extended or adjusted under 35 U.S.C. 154(b) by 94 days.

(21) Appl. No.: 11/071,958

(22) Filed: Mar. 4, 2005

(51) Int. Cl.
*A01H 5/00* (2006.01)

(52) U.S. Cl. ..... Plt./307
(58) Field of Classification Search ..... Plt./307
See application file for complete search history.

*Primary Examiner*—Kent Bell
*Assistant Examiner*—Annette H Para
(74) *Attorney, Agent, or Firm*—Jondle & Associates P.C.

(57) ABSTRACT

A Poinsettia cultivar particularly distinguished by its deep red bract color without any bluish tint, dark green leaves with moderate lobes, and medium-sized bracts arranged in a tight and nearly flat rosette is disclosed.

1 Drawing Sheet

Figure 1:
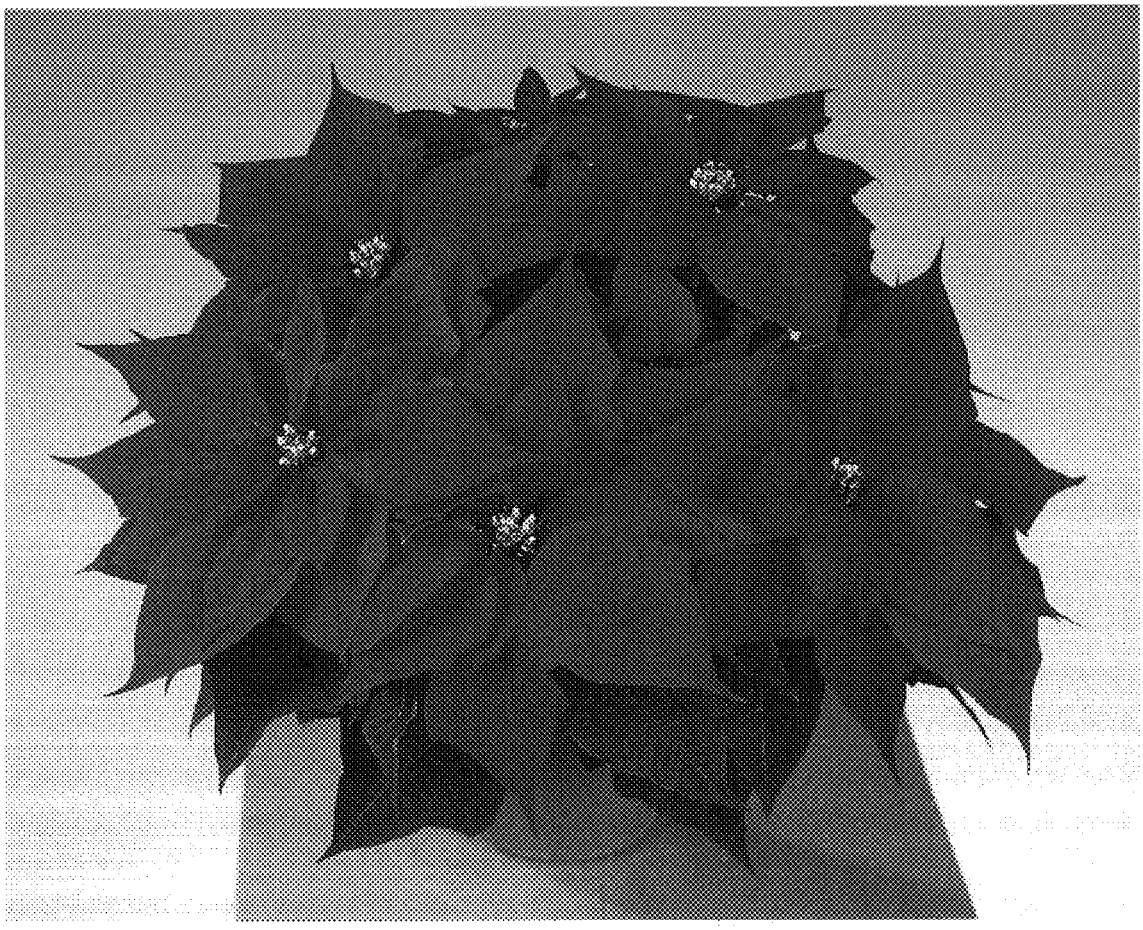

Genus and species: *Euphorbia pulcherrima* (Willd.).
Variety denomination: 'Fisnovired'.

BACKGROUND OF THE NEW PLANT

The present invention relates to a new and distinct cultivar of Poinsettia plant, botanically known as *Euphorbia pulcherrima* (Willd.), and hereinafter referred to by the name 'Fisnovired'. The new cultivar is a product of a planned breeding program which had the objective of creating new Poinsettia cultivars with red flower color in combination with dark-green foliage and good cultivation ability. 'Fisnovired' was originated from a hybridization made in Hillscheid, Germany in 1999.

The female parent was the Poinsettia cultivar 'Fisson' (U.S. Plant Pat. No. 9,365), characterized by red bract color and dark-green foliage with pointed lobes. The male parent was the Poinsettia cultivar 'Fismille' (U.S. Plant Pat. No. 13,660), characterized by bright red bracts, dark-green foliage, and relatively early flowering.

The seeds obtained from this hybridization were germinated in the early spring of 2000, and the resulting seedlings were selected during their flowering period in December 2000. In the spring of 2001, cuttings were taken from a single plant. These cuttings were grafted onto rootstocks of variety 'Beckmann's Altrosa' (U.S. Plant Pat. No. 9,336), which is also known as 'Maren,' in order to induce better branching ability. From the upper area of the successfully grafted plants, shoot tip cuttings were taken for the cultivation of branched plants for the second examination in the fall of 2001. The trial was repeated in the late summer and in the fall of 2002.

Horticultural examination of the clone starting in 2001 and continuing thereafter has confirmed that the combination of characteristics as herein disclosed for 'Fisnovired' are firmly fixed and retained through successive generations of asexual reproduction.

The following traits have been repeatedly observed and are determined to be the basic characteristics of 'Fisnovired' which in combination distinguish this Poinsettia as a new and distinct cultivar:

deep red bract color without any bluish tint ovate to weakly oak-shaped bracts medium sized bracts arranged in a tight and nearly flat rosette dark green leaves with moderate lobes medium sized, very well-branched and rounded plant habit suitable both for early culture and for the desirable late fall flowering beginning of flowering mid-season or somewhat earlier.

DESCRIPTION OF PHOTOGRAPH

This new Poinsettia plant is illustrated by the accompanying photograph which shows the plant's form, foliage and flowers. The colors shown are as true as can be reasonably obtained by conventional photographic procedures.

FIG. 1 shows overall plant habit including foliage and flowers.

DESCRIPTION OF THE NEW CULTIVAR

'Fisnovired' has not been observed under all possible environmental conditions. The phenotype may vary significantly with variations in environment such as temperature, light intensity, and day-length. The following observations, measurements and comparisons describe plants grown in Hillscheid, Germany under greenhouse conditions which approximate those generally used in commercial practice.

The plants described were grown in a greenhouse in Hillscheid, Germany from the summer to the fall of 2004. Rooted cuttings were planted in 14 cm pots on Jul. 22, 2004 and were pinched on August 6, which left 7–8 leaves remaining. Initially, the minimum temperature was 18° C. Beginning October 1, the temperature was lowered to a minimum temperature of 16 to 17° C. The plants initiated flowers under natural short-day conditions in fall. No black cloth was applied to the greenhouse to simulate short-day conditions. No growth regulator was applied.

Observations and measurements were mainly taken in early to mid-December when the plants were in full flower and about 20 weeks old. In the following description, color references are made to The Royal Horticultural Society Colour Chart (R.H.S.). The color references were determined indoors in a north light.

DESCRIPTION OF THE NEW PLANT

Classification:

*Family.*—Euphorbiaceae.

*Botanical.*—*Euphorbia pulcherrima* (Willd. Ex Klotzsch).

Parentage:

*Female parent.*—Poinsettia cultivar 'Fisson' (U.S. Plant Pat. No. 9,365).

*Male parent.*—Poinsettia cultivar 'Fismille' (U.S. Plant Pat. No. 13,660).

Growth:

*Time to produce a rooted cutting.*—About 20 days in a greenhouse at a temperature of 22–24° C.

*Blooming habit.*—Beginning under natural short-day conditions in fall: Botanically (cyathia open): around December 1. Commercially (bracts colored, marketable): in late November.

*Flowering response time.*—About 9 weeks.

*Flowering season.*—Mainly from late November to late December.

*Keeping quality.*—Good quality is maintained for about 4–5 weeks.

Plant:

*Form.*—Shrub, self-branching.

*Growth habit.*—Medium vigor, moderately compact structure; pinched plants are bushy with the branches upright-directed at an angle of roughly 45°; foliage canopy uniformly rounded.

*Height in 14 cm pot.*—25.0 cm as measured from soil line.

*Width.*—45.5 cm.

*Average number of branches.*—7.9.

*Length of branches.*—20–25 cm.

*Diameter of branches.*—0.4–0.6 cm.

*Average number of inflorescences.*—7.3.

Stems:

*Stem color.*—Middle part: RHS 143B (green). Upper part: RHS 137A (green).

Leaves:

*Quantity.*—50–55 leaves per plant.

*Shape.*—Ovate.

*Base.*—Rounded to obtuse.

*Apex.*—Acuminate.

*Lobes.*—Moderate.

*Margin.*—Entire, apart from the lobes.

*Texture.*—Upper surface: Smooth and flat, only weakly veined. Lower surface: Flat and smooth, except for the slightly protruding midrib and finer side veins in a pinnate pattern.

*Vein color.*—Upper surface: RHS 139C (green). Lower surface: RHS 139D (green).

*Size.*—Length: 12.7 cm. Width: 10.0 cm.

*Color.*—Mature foliage: Upper surface: Near RHS 139A. Lower surface: RHS 139B. Immature foliage: Upper surface: RHS 137B. Lower surface: RHS 137D.

*Leaf petiole.*—Length: 7.3 cm. Color: Upper surface: RHS 184B (purple). Lower surface: RHS 182C (light brownish-pink).

*Aspect.*—Petioles are horizontally- to slightly upwardly-directed, while the leaf blades are more or less horizontally-directed.

Inflorescence:

*Whole inflorescence with surrounding bracts.*—Medium to large sized, star-shaped, flat, with the bracts horizontally-directed in a tight arrangement, and overlapping.

*Diameter.*—26 cm.

*Height of inflorescence.*—2.5 cm.

Bracts:

*Number of bracts per inflorescence.*—13–15.

*Shape.*—Ovate.

*Base.*—Rounded.

*Apex.*—Acuminate.

*Lobes.*—Moderate.

*Size.*—Length: 13.5–14.5 cm. Width: 7.5 cm.

*Texture.*—Flat and smooth, very little rugosity with maturing of the bract.

*Vein color.*—Upper surface: Corresponds closely to the bract color. Lower surface: RHS 159A (white).

*Bract color.*—Upper surface: Between RHS 46B and RHS 46C. Lower surface: RHS 52A.

*Petiole.*—Length: 1–2 cm. Color: Upper surface: RHS 46A (red). Lower surface: Near RHS 159A (white).

Cyme:

*Cyme.*—Diameter: 1.5–2.2 cm.

*Cyathia number.*—5–8 borne in a tight cluster.

*Cyathium.*—Shape: Ovate. Diameter: 0.4–0.5 cm. Color: RHS 143B (green), top is RHS 45A (red).

*Peduncle.*—Color: RHS 143C (green). Length: 0.3 cm.

*Nectar cups.*—Number: One or two per cyathium. Size: 0.4 cm wide. Color: RHS 12A (yellow).

Reproductive organs:

*Stamens.*—Number: 10–20 in a cluster. Filaments: Length: 0.3 cm. Color: RHS 46A (red). Pollen: Quantity: Moderate. Color: RHS 14A (yellow).

*Ovary.*—Diameter: 0.3–0.4 cm. Length: 0.4 cm. Color: RHS 143A (green).

*Style.*—Length: 0.5 cm. Color: RHS 46B (red).

*Stigma.*—Shape: 6-lobed. Color: RHS 46A (red).

*Seeds.*—None observed.

Disease and insect resistance: No observations made.

COMPARISON WITH KNOWN CULTIVARS

The most similar cultivars in comparison to 'Fisnovired' are the varieties 'Fisson' (U.S. Plant Pat. No. 9,365), and 'Fiscor' (U.S. Plant Pat. No. 9,364). In comparison to 'Fisson', 'Fisnovired' has a similar bract color, but the bracts and leaves show less distinct lobes. Furthermore, 'Fisnovired' has a more even plant habit in early culture. Under high temperature 'Fisnovired' does not tend to develop long branches nor does heat delay flowering.

In comparison to 'Fiscor', 'Fisnovired' has a red bract color without any bluish hue, has somewhat more distinctly oak-shaped bracts and leaves, is more freely branching with thinner branches, has a rounder, narrower plant habit, and has somewhat earlier flowering.

I claim:

1. A new and distinct cultivar of Poinsettia plant as shown and described herein.

* * * * *